(12) United States Patent
Melius

(10) Patent No.: US 7,175,727 B2
(45) Date of Patent: Feb. 13, 2007

(54) SHAPED ABSORBENT PADS AND ASSOCIATED METHOD FOR MAKING

(75) Inventor: Shannon Melius, Appleton, WI (US)

(73) Assignee: Kimberley-Clark Worldwide, Inc., Neenah, WI (US)

( * ) Notice: Subject to any disclaimer, the term of this patent is extended or adjusted under 35 U.S.C. 154(b) by 89 days.

(21) Appl. No.: 10/233,168

(22) Filed: Aug. 30, 2002

(65) Prior Publication Data

US 2004/0044322 A1    Mar. 4, 2004

(51) Int. Cl.
    B32B 37/00    (2006.01)
    A61F 13/15    (2006.01)

(52) U.S. Cl. ............ 156/229; 156/160; 156/161; 156/162; 156/163; 156/164; 156/251; 156/256; 156/269; 604/369; 604/385.01; 604/385.23

(58) Field of Classification Search ........ 156/160–164, 156/229, 251, 256, 269; 604/369, 385.01, 604/385.23
    See application file for complete search history.

(56) References Cited

U.S. PATENT DOCUMENTS

| | | | |
|---|---|---|---|
| 3,296,351 A | 1/1967 | Rasmussen | |
| 3,808,639 A | 5/1974 | Tautvaisas | |
| 3,902,230 A | 9/1975 | Schwarz | |
| 4,116,892 A | 9/1978 | Schwarz | |
| 4,223,059 A | 9/1980 | Schwarz | |
| 4,276,336 A * | 6/1981 | Sabee | 428/132 |
| 4,285,100 A | 8/1981 | Schwarz | |
| 4,285,747 A | 8/1981 | Rega | |
| 4,381,782 A | 5/1983 | Mazurak et al. | |
| 4,655,760 A | 4/1987 | Morman et al. | |
| 4,921,643 A | 5/1990 | Walton et al. | |
| 5,167,897 A * | 12/1992 | Weber et al. | 264/288.8 |
| 5,560,793 A | 10/1996 | Ruscher et al. | |

(Continued)

FOREIGN PATENT DOCUMENTS

DE    1049051    1/1959

(Continued)

OTHER PUBLICATIONS

EPO Search Report, Sep. 4, 2003.

(Continued)

*Primary Examiner*—Melvin Mayes
*Assistant Examiner*—Kimberly McClelland
(74) *Attorney, Agent, or Firm*—Dority & Manning, P.A.

(57) ABSTRACT

A method for making absorbent pads for various absorbent articles is provided. A strip of the absorbent web material is conveyed along a machine direction, the absorbent web material having a generally first constant cross-direction width and generally first uniform basis weight. Longitudinally defined portions of the web material are stretched in the cross direction so as to define longitudinal sections having a wider cross-direction width and decreased basis weight alternately spaced between longitudinally extending sections of the web material having a lesser cross-direction width and greater basis weight. The web is released eventually cut in a cross direction into individual absorbent pads such that each pad has a crotch section corresponding to the longitudinal section having the lesser cross-direction width and greater basis weight and at least one of a front section and back section corresponding to the wider cross-direction width and decreased basis weight.

7 Claims, 7 Drawing Sheets

U.S. PATENT DOCUMENTS

| | | | |
|---|---|---|---|
| 5,597,437 A | 1/1997 | Lange et al. | |
| 5,601,544 A | 2/1997 | Glaug et al. | |
| 5,626,571 A * | 5/1997 | Young et al. | 604/370 |
| 5,645,542 A | 7/1997 | Anjur et al. | |
| 5,653,842 A | 8/1997 | Kuen | |
| 5,695,846 A | 12/1997 | Lange et al. | |
| 5,728,085 A | 3/1998 | Widlund et al. | |
| 5,730,737 A | 3/1998 | Widlund et al. | |
| 5,814,034 A | 9/1998 | Widlund et al. | |
| 5,818,719 A | 10/1998 | Brandon et al. | |
| 5,928,452 A * | 7/1999 | McFall et al. | 156/269 |
| 5,932,039 A | 8/1999 | Popp et al. | |
| 5,964,970 A | 10/1999 | Woolwine et al. | |
| 6,033,502 A | 3/2000 | Coenen et al. | |
| 6,183,587 B1 * | 2/2001 | McFall et al. | 156/201 |
| 6,214,274 B1 * | 4/2001 | Melius et al. | 264/280 |
| 6,355,200 B1 * | 3/2002 | Schmidt et al. | 264/286 |
| 6,362,389 B1 | 3/2002 | McDowall et al. | |
| 6,383,431 B1 * | 5/2002 | Dobrin et al. | 264/154 |
| 6,410,820 B1 * | 6/2002 | McFall et al. | 604/369 |
| 2002/0105110 A1 | 8/2002 | Dobrin et al. | |

FOREIGN PATENT DOCUMENTS

| | | |
|---|---|---|
| EP | 0449548 A2 | 10/1991 |
| EP | 0650714 A1 | 5/1995 |
| EP | 0810078 | 12/1997 |
| WO | 9301784 | 2/1993 |

OTHER PUBLICATIONS

Written Opinion Cited by EPO in Corresponding PCT Application.

* cited by examiner

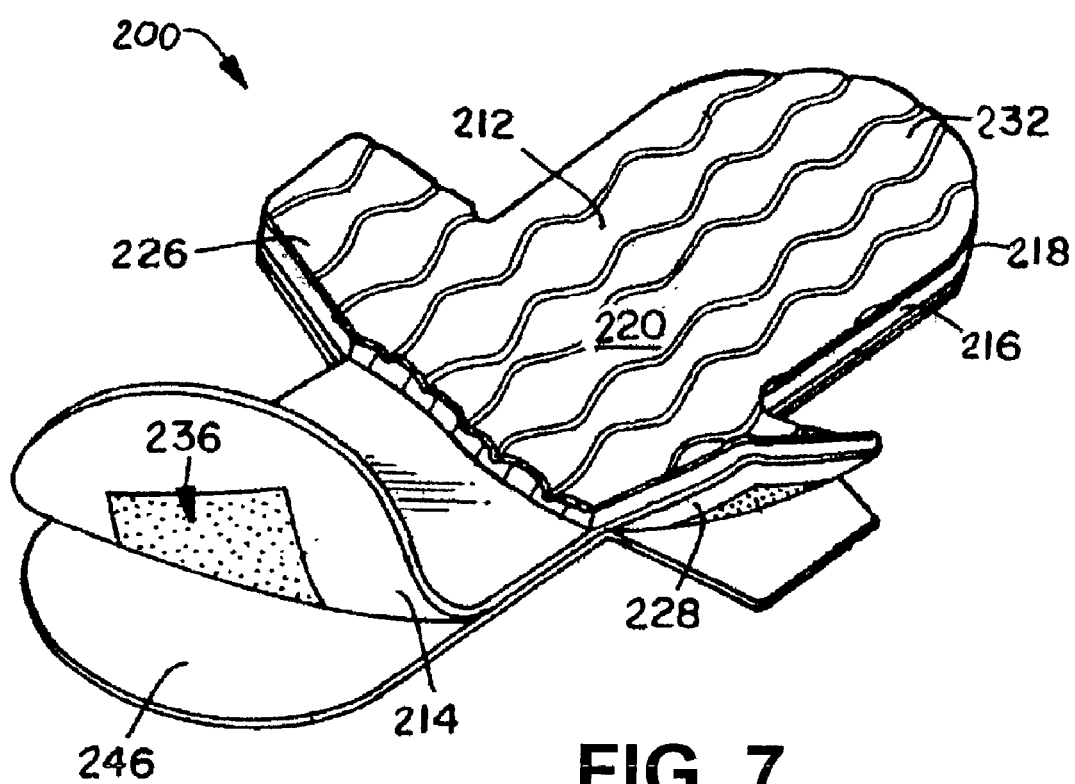

SHAPED ABSORBENT PADS AND ASSOCIATED METHOD FOR MAKING

TECHNICAL FIELD OF THE INVENTION

The present invention relates generally to the field of forming shaped absorbent pad structures from an absorbent web, the pads intended for use in disposable absorbent articles such as diapers, child's training pants, feminine care articles, incontinence articles, swim pants, and the like.

BACKGROUND

Many types of disposable consumer products such as diapers, training pants, feminine care articles, incontinence articles, and the like, utilize an absorbent pad structure for absorbing and wicking away bodily fluids. The absorbent pads are conventionally formed from an absorbent web, typically a non-woven fibrous web material. With one particular general practice, the absorbent web is formed by employing conventional airlaying techniques wherein fibers and typically a superabsorbent material are mixed and entrained in an air stream and then directed onto a forming surface to form the web. The absorbent web may then be directed for further processing and assembly with other components to produce a final absorbent article. An advantage of this practice is that trim waste can be immediately recycled by returning the waste to the upstream fiberizing equipment and/or airlaying equipment.

With another conventional technique, preformed absorbent web sheets or layers are delivered into a manufacturing line from a preformed supply, such as a supply roll. The absorbent sheet material may be separated into adjacent strips having various configurations of repeat pattern "nested" shaped pads wherein the shape of one pad is substantially nested with the shape of at least one immediately adjacent pad.

The preformed absorbent material roll process presents particular challenges. For example, the geographical separation of the base roll-making machine makes recycling of the trim waste impractical and cost prohibitive. In this regard, the nesting feature mentioned above has been desirable to reduce the amount of waste that is generated from the originally supplied (roll) of absorbent web. However, with conventional nesting techniques and profiles, a considerable amount of trim waste is still generated.

Also, the more easily processed strip-shapes have a repeat pattern that is substantially symmetrical with respect to its longitudinal dimension that coincides with the machine direction of the web. With such longitudinally-symmetric nested patterns, a single cycle of the repeat pattern provides an individual web segment wherein the shape of a first lengthwise half portion of the segment substantially matches the shape of the longitudinally opposed other half portion. However, for certain consumer absorbent articles, it has been found desirable from a product fit, comfort, and performance standpoint to shape the pad so that it is longitudinally asymmetric. For example, the pad may have a wider front or "ear" portion as compared to the back portion. Unfortunately, such configurations in a nested pattern add to the amount of generated waste.

Also, it may be desirable to provide a higher basis weight of absorbent material in the crotch portion as compared to the front and back portions. This has conventionally been done by folding or otherwise adding additional absorbent material (e.g., additional layers) into the crotch area.

The present invention provides a method for producing longitudinally symmetric or asymmetric absorbent pad structures in a roll process with minimal or zero waste of the roll material.

SUMMARY OF THE INVENTION

Objects and advantages of the invention will be set forth in part in the following description, or may be obvious from the description, or may be learned through practice of the invention.

The present invention provides an improved method for making absorbent pads for use in various applications of consumer disposable absorbent articles, such as disposable diapers, child's training pants, feminine care articles including but not limited to interlabial products, incontinence articles, swim pants, and the like. The pads may be longitudinally symmetric or asymmetric. With asymmetric pads, the back portion has a different shape or configuration as compared to the front portion of the pad. As mentioned, in certain applications, longitudinally asymmetric pads of this type may be desirable with respect to product fit, comfort, and performance as compared to longitudinally symmetric pads. The pads may be longitudinally symmetric in that the front and back portions have generally the same shape. Such longitudinally symmetric pads may be more than adequate and desirable in certain applications, and may be desirable from an ease of manufacturing standpoint. The pads may have a center or intermediate portion being wider than the longitudinal ends of the pad. The present method provides a technique for mass producing such pads from a continuous strip of absorbent web material in a manner so that there is virtually zero waste of the web material.

In accordance with one embodiment of the present method for making absorbent pads, an absorbent web material is delivered in a machine-direction flow in the form of a continuous strip, for example from a supply roll. In other words, the parallel sides of the strip of material lie in the machine-direction. The web material strip has a generally constant machine-direction width and a generally uniform basis weight. Longitudinally defined portions of the strip are selectively stretched in the cross-direction so as to define longitudinal sections having a wider cross-directional width and lower basis weight alternately spaced between longitudinally extending sections of the web material having a lesser cross-directional width and greater basis weight. The sections having the lesser cross-directional width may or may not correspond to "unstretched" sections of the supplied web strip. The web material is released from the stretching action and eventually the strip of web material is cut into individual absorbent pads wherein each pad has at least one longitudinally extending section of the wider cross-directional width and decreased basis weight. For example, the crotch section of each pad may correspond to the longitudinal section having the lesser cross-directional width and greater basis weight (e.g., the original cross-directional width and basis weight), and either one or both of a front section and back section corresponding to the wider cross-directional width and lower basis weight.

The absorbent pads may be longitudinally symmetric wherein the back and front sections have generally the same shape and basis weight, for example as with a "dog-bone" shape. In this embodiment, the stretched longitudinal sections of the web strip are cross-directionally cut at the mid point (as measured in the machine direction) to define the individual pad structures.

In an alternate embodiment, the absorbent pads may be longitudinally asymmetric wherein the front section contains relatively wider "ears" as compared to the back section. The stretched longitudinally extending sections of the strip (prior to being cut into individual pads) would thus not be uniform. For example, stretched sections having a first width and first basis weight would alternate (with unstretched sections therebetween) with stretched sections having a second lesser width and second greater basis weight as compared to the first width and basis weight. The first width sections would be cross-directionally cut at their mid-point to define the "front" portion of respective adjacent serial pads, and the second width sections would be cross-directionally cut at their mid-point to define the back portion of respective adjacent serial pads.

In an alternate embodiment, such as a feminine care incontinence pad or menstrual pad, it may be desirable to form "wings" in the middle of the pad in accordance with the present invention in which a wider, stretched portion is nearer the middle of the pad than the ends. This wing may be wrapped around the wearer's undergarment for additional leakage protection.

After being stretched into longitudinally spaced sections having a desired configuration and basis weight, the strip can be conveyed in the machine-direction to an in-line process wherein the pads are eventually cut, spaced, rotated if necessary, and placed in an absorbent article. In an alternate embodiment, the strip may be stored in an appropriate form for subsequent use in an in-line manufacturing process. For example, the strip may be rolled into a supply roll, or folded and stacked in a festooned configuration.

The strip of web material may be stretched by various methods. In one particular embodiment, the web material is passed between rolls having a defined pattern of intermeshing grooves and ridges at locations corresponding to the stretched sections of the web. As the web material is engaged by the grooves and ridges, it is stretched due to the increased effective cross-directional path resulting from the intermeshing of the grooves and ridges. Once the web material is passed beyond the rolls and "flattens out," the web strip will have an increased cross-directional width along the longitudinal portions engaged by the rolls. In an alternate embodiment, the web material may be clamped or otherwise gripped at selected positions along its machine direction sides and pulled in the cross-direction along selected longitudinal sections so as to increase the cross-direction width and decrease the basis weight in such sections. This process may be carried out, for example, by a modified tenter-frame device.

The invention is not limited to any particular type of absorbent web material, the only requirement being that the web have sufficient stability to undergo the stretching action and retain or "hold" the resulting stretched configuration. The web material may be, for example, an air laid material with binder fibers, a coform, a foam, and the like. Various suitable materials are well known to those skilled in the art.

In one particular embodiment, the absorbent web material is generally non-elastic such that it retains its stretched configuration after being released from the stretching action without a subsequent setting step. In an alternate embodiment, however, the web material may be generally elastic, such as a suitable absorbent elastic coform, and the stretched shape is "set" prior to releasing the material from the stretching action. For example, heat may be applied to the web in the stretched state sufficient for setting the thermoplastic elastic components of the web material. In the embodiment wherein the grooved rolls are used to stretch the material, the rolls may be heated so as to simultaneously set the stretched configuration. Heat from the rolls may also soften the web material (e.g., the thermoplastic material in the web coform) and thus enhance the stretching process. Alternatively, the web may be subjected to a steam bath, or any other suitable process for applying sufficient heat to thermally set the stretched shape prior to releasing the web material. The web material may alternately be treated with an energy source, such as microwave, ultrasonic, or ultraviolet radiation, for activating binder materials that set the stretched shape. The web material may alternatively be sprayed with an adhesive or other material to permanently or temporarily "set" or hold the web material in its stretched configuration. The adhesive may be a temporary adhesive that "releases" upon being wetted in the absorbent article such that the stretched area of the pad would tend to contract somewhat after being wetted and provide, for example, an enhanced gasketing at the waist. Alternatively, the stretched web may be laminated or otherwise fixed to another material prior to release from stretching.

The present invention also includes various embodiments of absorbent pads that are manufactured according to the method set forth herein, as well as absorbent articles incorporating such pads.

The inventions will be described below in greater detail by reference to particular embodiments set forth in the figures.

BRIEF DESCRIPTION OF THE FIGURES

FIG. 7 is a perspective and partial cutaway view of an alternate representative absorbent article incorporating an absorbent pad in accordance with the invention.

DETAILED DESCRIPTION

Figure 1:
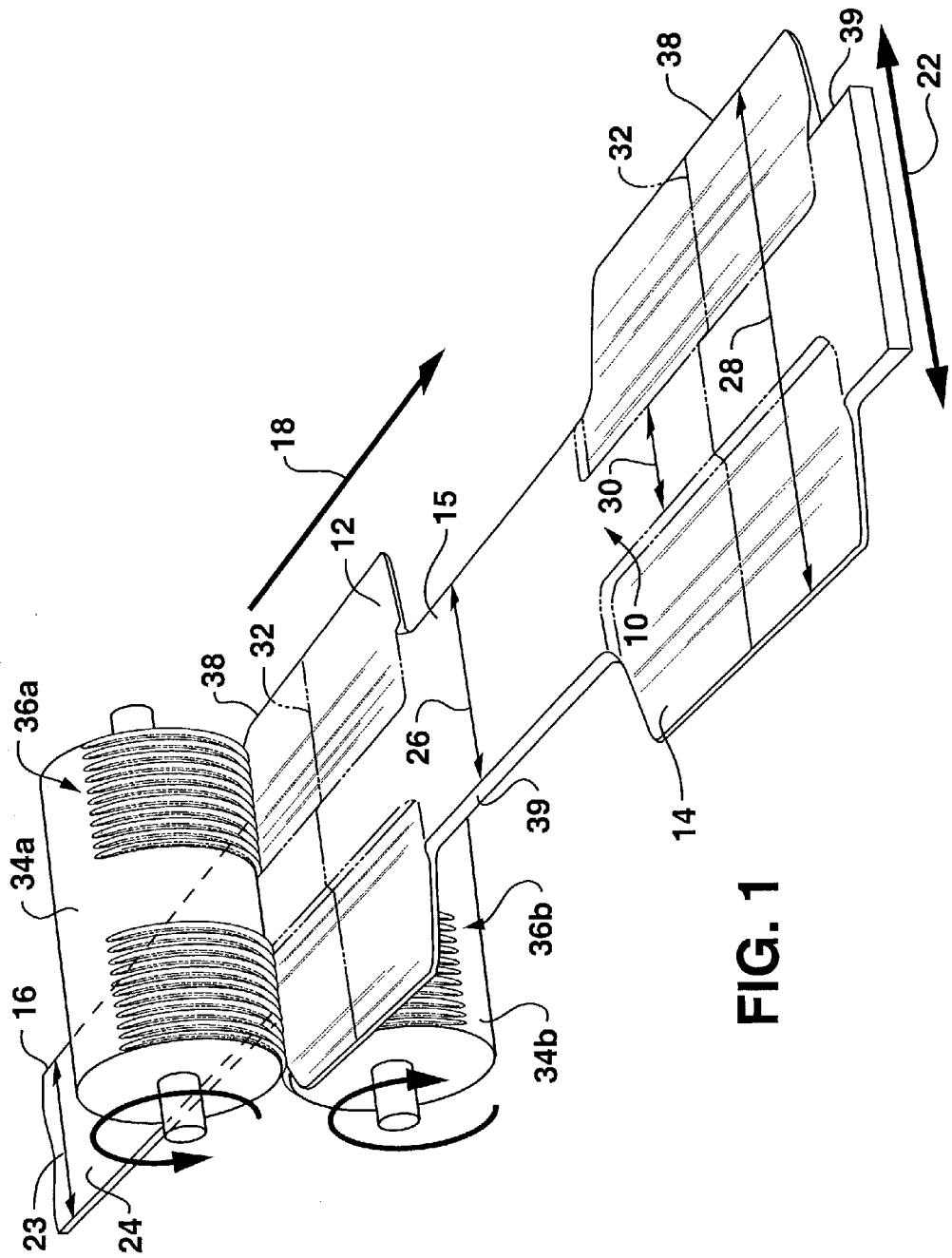
FIG. 1 is a partial perspective view of an embodiment for stretching an absorbent web material according to the invention using a grooved roll configuration.

The invention will now be described in detail with reference to particular embodiments thereof. The embodiments are provided by way of explanation of the invention, and not meant as a limitation of the invention. For example, features described or illustrated as part of one embodiment may be used with another embodiment to yield still a further embodiment. It is intended that the present invention include these and other modifications and variations as come within the scope and spirit of the invention.

The present method is particularly suited for the manufacture of pad structures from a web of absorbent material, the pads intended for use in various consumer disposable absorbent products. Such products include, but are not limited to, diapers, child's training pants, feminine care articles (such as panty liners, pads, and interlabial products), incontinence articles, swim pants, and the like. The invention is not limited to any particular type or composition of absorbent web material, and may be practiced with any suitable absorbent web material known to those skilled in the art. The absorbent web material may include any structure and combination of components which are generally compressible, conformable, non-irritating to a wearer's skin, and capable of absorbing and retaining liquids and certain body wastes.

For example, the absorbent web material may include cellulosic fibers (e.g., wood pulp fibers), other natural fibers, synthetic fibers, woven or nonwoven sheets, scrim netting or other stabilizing structures, superabsorbent material, binder materials, surfactants, selected hydrophobic materials, pigments, lotions, odor control agents or the like, as well as combinations thereof. In a particular embodiment, the absorbent web material is a matrix of cellulosic fluff and superabsorbent hydrogel-forming particles. The cellulosic fluff may comprise a blend of wood pulp fluff. One preferred type of fluff is identified with the trade designation CR 1654, available from US Alliance Pulp Mills of Coosa, Ala., USA, and is a bleached, highly absorbent wood pulp containing primarily soft wood fibers. As a general rule, the superabsorbent material is present in the absorbent web in an amount of from about 0 to about 90 weight percent based on total weight of the web. The web has a density within the range of about 0.10 to about 0.50 grams per cubic centimeter.

Superabsorbent materials are well known in the art and can be selected from natural, synthetic, and modified natural polymers and materials. The superabsorbent materials can be inorganic materials, such as silica gels, or organic compounds, such as crosslinked polymers. Typically, a suberabsorbent material is capable of absorbing at least about 15 times its weight in liquid, and desirably is capable of absorbing more than about 25 times its weight in liquid. Suitable superabsorbent materials are readily available from various suppliers. For example, FAVOR SXM 880 superabsorbent is available from Stockhausen, Inc., of Greensboro, N.C., USA; and Drytech 2035 is available from Dow Chemical Company, of Midland Mich., USA.

Subsequent to or after being cut from the web material strip, the individual absorbent pads may be partially or wholly wrapped or encompassed by a suitable tissue or nonwoven wrap that aids in maintaining the integrity and shape of the pad.

The absorbent materials may be formed into a web structure by employing various conventional methods and techniques. For example, the absorbent web may be formed with a dry-forming technique, an airlaying technique, a carding technique, a meltblown or spunbond technique, a wet-forming technique, a foam-forming technique, or the like, as well as combinations thereof. Layered and/or laminated structures may also be suitable. Methods and apparatus for carrying out such techniques are well known in the art.

The absorbent web material may also be a coform material. The term "coform material" generally refers to composite materials comprising a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff and also superabsorbent particles or fibers, inorganic absorbent materials, treated polymeric staple fibers and the like. Any of a variety of synthetic polymers may be utilized as the melt-spun component of the coform material. For instance, in some embodiments, thermoplastic polymers can be utilized. Some examples of suitable thermoplastics that can be utilized include polyolefins, such as polyethylene, polypropylene, polybutylene and the like; polyamides; and polyesters. In one embodiment, the thermoplastic polymer is polypropylene. Some examples of such coform materials are disclosed in U.S. Pat. No. 4,100,324 to Anderson, et al.; U.S. Pat. No. 5,284,703 to Everhart, et al.; and U.S. Pat. No. 5,350,624 to Georger, et al.; which are incorporated herein in their entirety by reference for all purposes.

It is also contemplated that elastomeric absorbent web structures may be particularly useful with the present invention. For example, an elastomeric coform absorbent structure having from about 35% to about 65% by weight of a wettable staple fiber, and greater than about 35% to about 65% by weight of an elastomeric thermoplastic fiber may be used to define absorbent pad structures according to the invention. Examples of such elastomeric coform materials is provided in U.S. Pat. No. 5,645,542, incorporated herein in its entirety for all purposes. As another example, a suitable absorbent elastic nonwoven material may include a matrix of thermoplastic elastomeric nonwoven filaments present in an amount of about 3 to less than about 20% by weight of the material, with the matrix including a plurality of absorbent fibers and a super-absorbent material each constituting about 20–77% by weight of the material. U.S. Pat. No. 6,362,389 describes such a nonwoven material and is incorporated herein by reference in its entirety for all purposes. Absorbent elastic nonwoven materials are useful in a wide variety of personal care articles where softness and conformability, as well as absorbency and elasticity, are important.

The absorbent web may also be a nonwoven web comprising synthetic fibers. The web may include additional natural fibers and/or superabsorbent material. The web may have a density in the range of about 0.05 to about 0.5 grams per cubic centimeter. The absorbent web can alternatively be a foam.

In a particular aspect of the invention, the absorbent web material can be provided with an absorbent capacity of at least about 8 g/g employing 0.9 wt % saline (8 grams of 0.9 wt % saline per gram of absorbent web). The absorbent capacity of the absorbent web can alternatively be at least about 9 g/g, and can optionally be at least about 15 g/g to provide improved benefits. Additionally, the absorbent capacity may be up to about 40 g/g, or more, to provide desired performance.

In another aspect, the web of absorbent material can be provided with a tensile strength value of at least about 0.5 N/cm (Newtons per cm of "width" of the material, where the "width" direction is perpendicular to the applied force). The tensile strength of the absorbent web can alternatively be at least about 1.5 N/cm, and can optionally be at least about 2 N/cm to provide improved benefits. In another aspect, the web of absorbent material can be provided with a tensile strength value of up to a maximum of about 100 N/cm, or more. The tensile strength of the absorbent web can alternatively be up to about 10 N/cm, and can optionally be up to about 20 N/cm to provide improved benefits.

The selected tensile strength should provide adequate processability of the web throughout the manufacturing process, and can help to produce articles that exhibit desired combinations of softness and flexibility. In particular, the absorbent web material should have a tensile strength in the cross-direction to undergo stretching as described herein without resulting in substantial degradation of the web integrity to the extent that the pad structures cannot be further processed in absorbent articles. In some cases, the stretching of the web material in the cross direction can provide a softer and more flexible material than the initial web. This is generally desired for initially stiff materials such as some stabilized airlaid or wetlaid materials.

The absorbent material web is also selected so that the individual absorbent pad structures possess a particular individual total absorbency depending on the intended article of use. For example, for infant care products, the total absorbency can be within the range of about 200–900 grams of 0.9 wt % saline, and can typically be about 500 g of 0.9 wt % saline. For adult care products, the total absorbency can be within the range of about 400–2000 grams of 0.9 wt % saline, and can typically be about 1300 g of saline. For feminine care products, the total absorbency can be within the range of about 7–50 grams of menstrual fluid or menses simulant, and can typically be within the range of about 30–40 g of menstrual fluid or menses simulant.

Aspects of the present method include delivering a supply of the absorbent web material in a machine-direction flow. The web material may be delivered in the form of a continuous ribbon or strip from a supply source, such as a roll. In an alternate embodiment, the web material may be supplied in the form of generally rectangular discrete sheets of fibrous material. Thus the term "web" is intended to include a continuous supply, such as from a roll, as well as a supply of discrete sheets of material. Optionally, the web strip may be supplied directly from an in-line manufacturing operation. The "machine-direction" is the direction along which the strip travels length-wise through a particular processing stage. The web material strip has a "cross-direction" or "width" that is perpendicular to the machine-direction. The material also has a depth-wise "z" direction that is perpendicular to the cross-direction and machine-direction.

As discussed, the present invention provides a method for making shaped absorbent pad structures for use in any number of disposable absorbent articles by stretching an initial strip of absorbent web material into a desired configuration for the pads. It should be appreciated that the invention is not limited to any particular type or composition of absorbent material, shape of the final absorbent pad structure, or intended absorbent article. Also, the invention is not limited to any particular methodology or device for applying a stretching force to the strip of absorbent web material. The examples of the methods and apparatus described herein are not limiting and are provided for purposes of conceptually explaining the invention to those of ordinary skill in the art.

Figure 2:
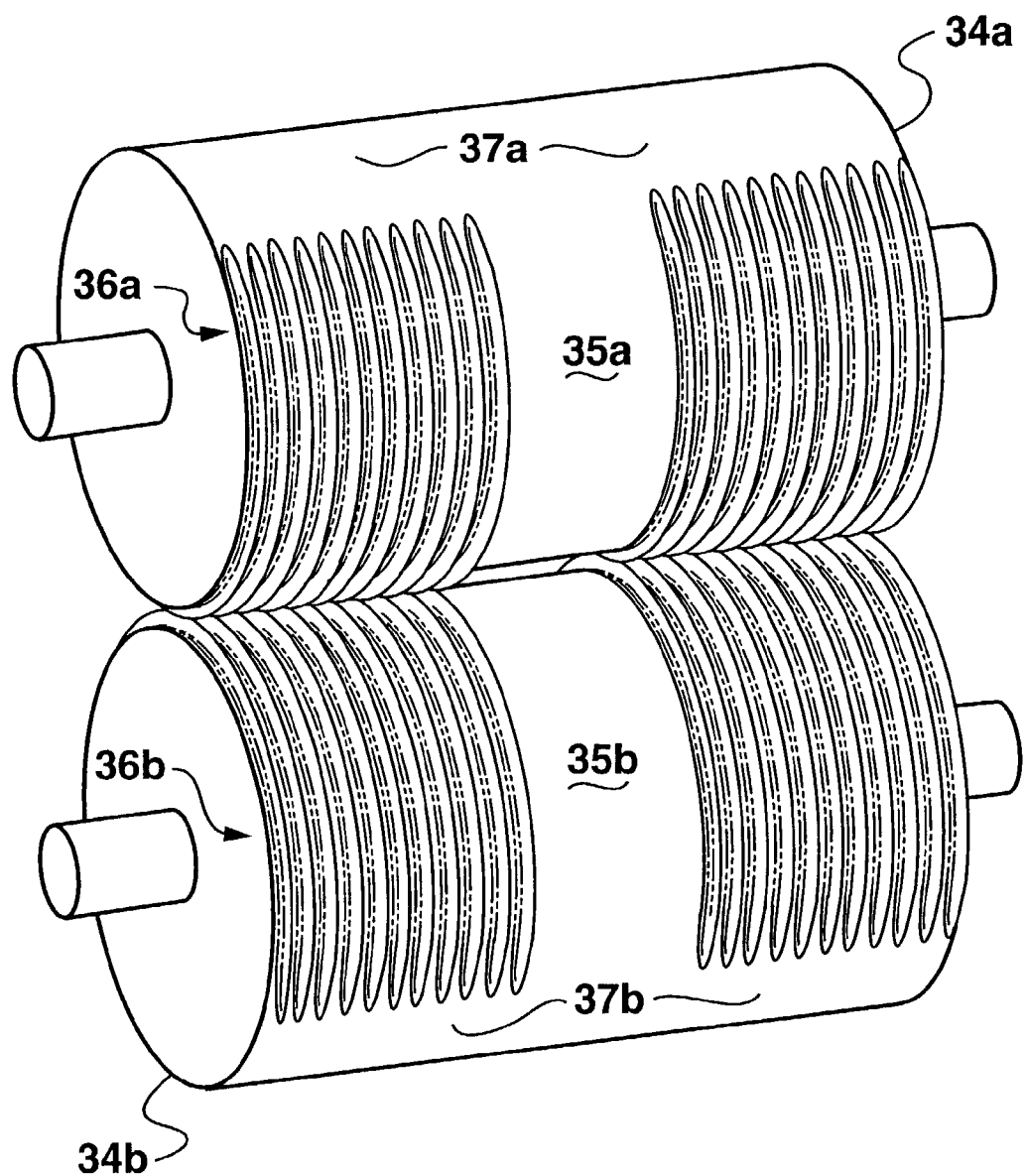
FIG. 2 is perspective view of a pair of rollers that may be used in a process for making absorbent pad structures according to the invention.

Referring to the figures in general, a conceptual illustration is provided of one method for making shaped absorbent pads according to the present invention. It should be understood that the dimensions, shape, and varying thickness of the absorbent pad structure 10 shown in the figures is exaggerated for sake of illustrating particular concepts and features of the invention. Referring to FIGS. 1 and 2, a web 16 of a suitable absorbent material is conveyed in the form of, for example, a strip or ribbon 24 having an initial cross-directional width 23 and basis weight. The web 16 is conveyed in a machine direction 18 and has a cross-direction 22. As discussed, any number of combinations of materials may be used as the absorbent web material 16. The web material may be supplied in the form of discrete sheets of material, as mentioned above. A limitation on the web material 16 is, however, that it be "substantial" enough to undergo the stretching operation. The web material strip 24 should also have an initial basis weight so that the final shaped pad structure 10 has a desired absorbency in all areas. For example, the initial web material strip 24 may have a basis weight of at least about 50 gsm (grams per square meter). Alternatively, the initial web material strip 24 may have a basis weight of at least about 200 gsm, 500 gsm, 800 gsm, or 1200 depending on the end use requirements of the product.

It should also be appreciated that the initial web material strip need not have a uniform width or basis weight. The material strip 24 may have varying basis weight sections and may take on any number of non-uniform shapes and configurations.

The web material strip 24 is subsequently subjected to a cross-directional stretching action over longitudinally defined portions thereof. This stretching action produces a repeating pattern of longitudinal portions or sections 38 of the web material having a wider cross-directional width 28 and a decreased basis weight interspersed between portions 39 having a lesser cross-directional width and greater basis weight. In the illustrated embodiment, the portions 39 correspond to "unstretched" portions of the web material having a cross-directional width 26. However, in alternate embodiments, portions 39 may also be stretched to a lesser degree than portions 38, in which case the width 26 is greater than 23.

After release from the stretching operation, the shaped strip 24 can be cut in a cross-direction into individual pad structures 10 wherein each pad contains at least one longitudinal section having the greater cross-direction width and decreased basis weight. For example, referring to FIG. 1, the shaped strip can be cut at the mid-point of each stretched longitudinal portion 38 along lines 32. Each pad 10 thus has a crotch portion 15 corresponding essentially to the interspersed unstretched portions 39, a back or wing portion 12 defined by one-half (or other percentage) of the stretched longitudinal portion 38, and a front section 14 also defined by one-half (or other percentage) of the stretched longitudinal portion 38. Thus, in this embodiment, the individual pads are essentially longitudinally symmetric in that the back 12 and front 14 sections on either side of the crotch section 15 have the same shape and configuration. In one particular embodiment, the shaped pad 10 may have essentially a symmetric dog-bone configuration. Longitudinally symmetric pads 10 are defined when the stretched longitudinal portions 38 have a generally uniform cross-directional width 28 and machine-direction length.

It should be appreciated that the pad configuration shown in FIG. 1 is for illustrative purposes only. Various other pad configurations are achievable with the method of this invention. For example, each pad 10 may have the stretched longitudinal portion 38 as an intermediate or crotch section between unstretched longitudinal end portions. In another embodiment, the pads 10 may have the stretched portion 38 at only one end thereof, this end corresponding to either the front or back section of the pad.

One method for applying a stretching force to defined longitudinally extending portions of the strip 24 of web material is to pass the strip 24 between the nip of a pair of rollers 34a and 34b having a surface configuration configured to engage and increase the effective cross-directional length of the web material 16 by pulling or stretching the web material. For example, the rollers 34a and 34b may have intermeshing grooves/ridges 36a and 36b defined in a pattern corresponding to the shape and length of the stretched portions 38 of the web. The intermeshing grooves define a serpentine or sine-wave path therebetween having an increased effective length as compared to flat or smooth circumferential sections of the rollers. As the web material 16 is conveyed through the rollers 34a and 34b, the web material passing through the intermeshing grooves 36a and 36b is thus pulled and stretched in the cross direction. The degree of stretch, and thus increase in cross-directional width and decrease in web material basis weight, is a factor of the groove depth and web material properties. The machine-direction (longitudinal) length of the stretched portions is a factor of the circumferential length of the grooves 36a and 36b on the respective rollers. It may be conceptualized that, as the material 16 having a given width and thickness (basis weight) passes through the grooves, the material 16 is pulled or stretched into a series of accordion-like folds having a decreased thickness (basis weight). Once the material 16 exits the rollers, the folds "flatten" out and the material assumes a thinner and wider profile in the respective stretched portions.

It should be appreciated that the intermeshing grooves and ridges 36a and 36b need not be in the form of continuous circumferential rings as illustrated. The grooves and ridges 36a and 36b may, for example, define a pattern of discontinuous intermeshing regions, such as a checker-board or diamond pattern.

The rollers 34a and 34b may have a diameter such that more than one pad is processed with each revolution of the rollers. In this case, the grooves and ridges 36a and 36b would be spaced accordingly on the circumference of the rollers so as to generate a uniform series of stretched portions 38 as the web material is conveyed through the rollers.

Referring to FIG. 2, the rollers 34a and 34b may have relatively flat or "ungrooved" sections 35a and 35b between the pattern of grooves 36a and 36b. As can be particularly seen in FIG. 1, these sections correspond to the machine-direction centerline of the web strip and thus result in a relatively unchanged basis weight section 30 of the back 12 and front 14 sections of the web material along their centerlines. In other words, the back and front sections 12, 14 may have decreased basis weight "wing" portions extending from greater basis weight centerline portions 30 thereof. The spacing between the nip of the ungrooved sections 35a and 35b may be such that the web material 16 is flattened or compressed to a degree.

Although not illustrated in the figures, with another embodiment the grooves 36a and 36b could extend completely across the rollers 34a and 34b. With this embodiment, the stretched portions 38 would have a uniform cross-directional basis weight and even greater width. Alternatively, a fully or partially grooved roll could be raised and lowered intermittently to provide different depths of engagement.

Alternatively, with any of these arrangements, a multiple stage stretching may be desired in which the web is stretched in multiple stages or a combination of stretching methods or patterns. This could allow for maximum stretching of the material that might otherwise be limited by the available space in the grooved rolls, for example.

The ungrooved circumferential sections 37a and 37b of the rollers 34a and 34b result in the unstretched portions 39 or crotch section 15 of the pads 10. The nip spacing between these sections may be such that the web material 16 is flattened or compressed to some degree such that the crotch sections 15 have a cross-directional width 26 greater than the initial width 23 of the web strip 24. In another embodiment, the sections 37a and 37b may contain grooves that stretch the web to a lesser extent than the grooves 36a and 36b. Alternatively, the crotch sections 15 may have a width 26 generally equal to the width 23 of the web strip 24.

The methodology of stretching a web material in the cross-direction with grooved rollers is described in greater detail in U.S. Pat. Nos. 4,116,892; 4,285,100; and 4,223,059. These patents are incorporated herein by reference for all purposes. U.S. Pat. No. 6,214,274 B1 entitled PROCESS FOR COMPRESSING A WEB WHICH CONTAINS SUPERABSORBENT MATERIAL discloses examples of suitable circumferentially-grooved rollers and is incorporated herein by reference in its entirety for all purposes.

It should also be appreciated that other factors will effect the degree of cross-directional stretching of the web material. For example, tension may be applied to the web in the machine direction prior to, during, or after stretching the web in the cross-direction. This may also affect the length of the web. The machine direction tension may cause a necking-in of the material and reduction of the initial cross-direction width. Depending on the type of absorbent material, the cross-direction stretching may tend to set the necked condition. In an alternate embodiment, the web may be tensioned in the machine direction subsequent to the cross-direction stretching. This action may result in a necking in of the cross-direction stretched portions and unstretched portions of the web material. Those skilled in the art will understand that numerous combinations of factors may be varied to adjust or control the width of the stretched portions of the web material, as well as the length of the web material.

Figure 3A:
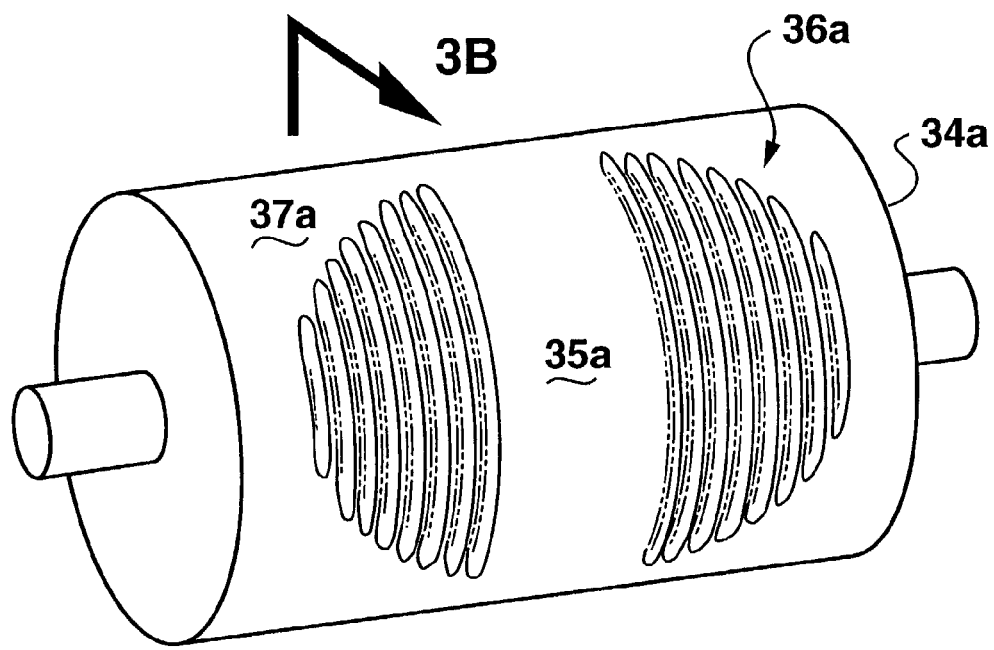
FIGS. 3A and 3B are perspective views of opposite sides of an alternate roll configuration that may be used for defining longitudinally asymmetric pads according to the invention.
Figure 3B:
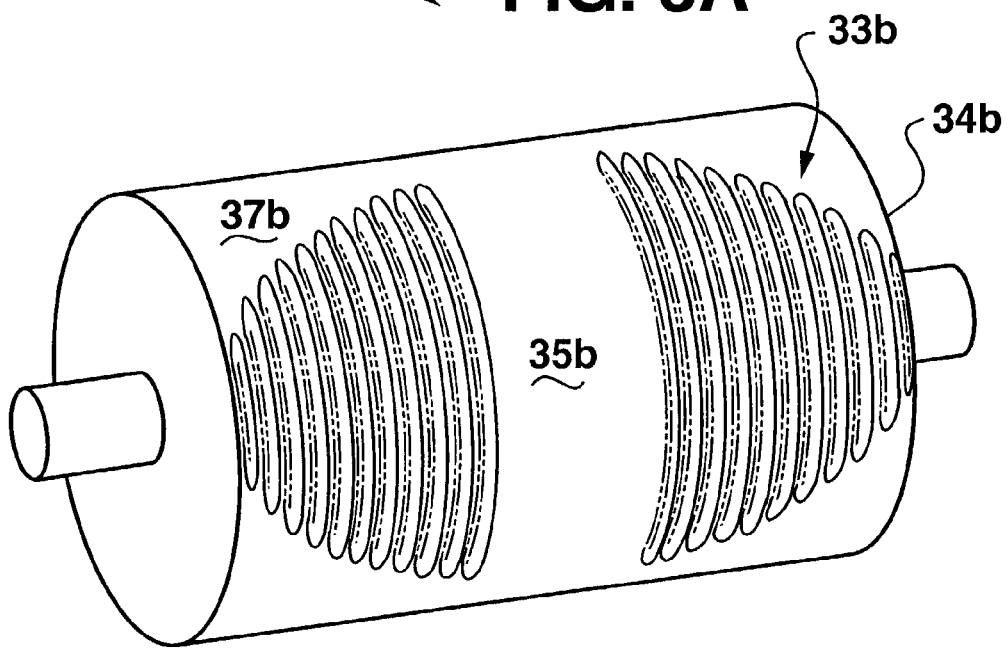
Figure 4:
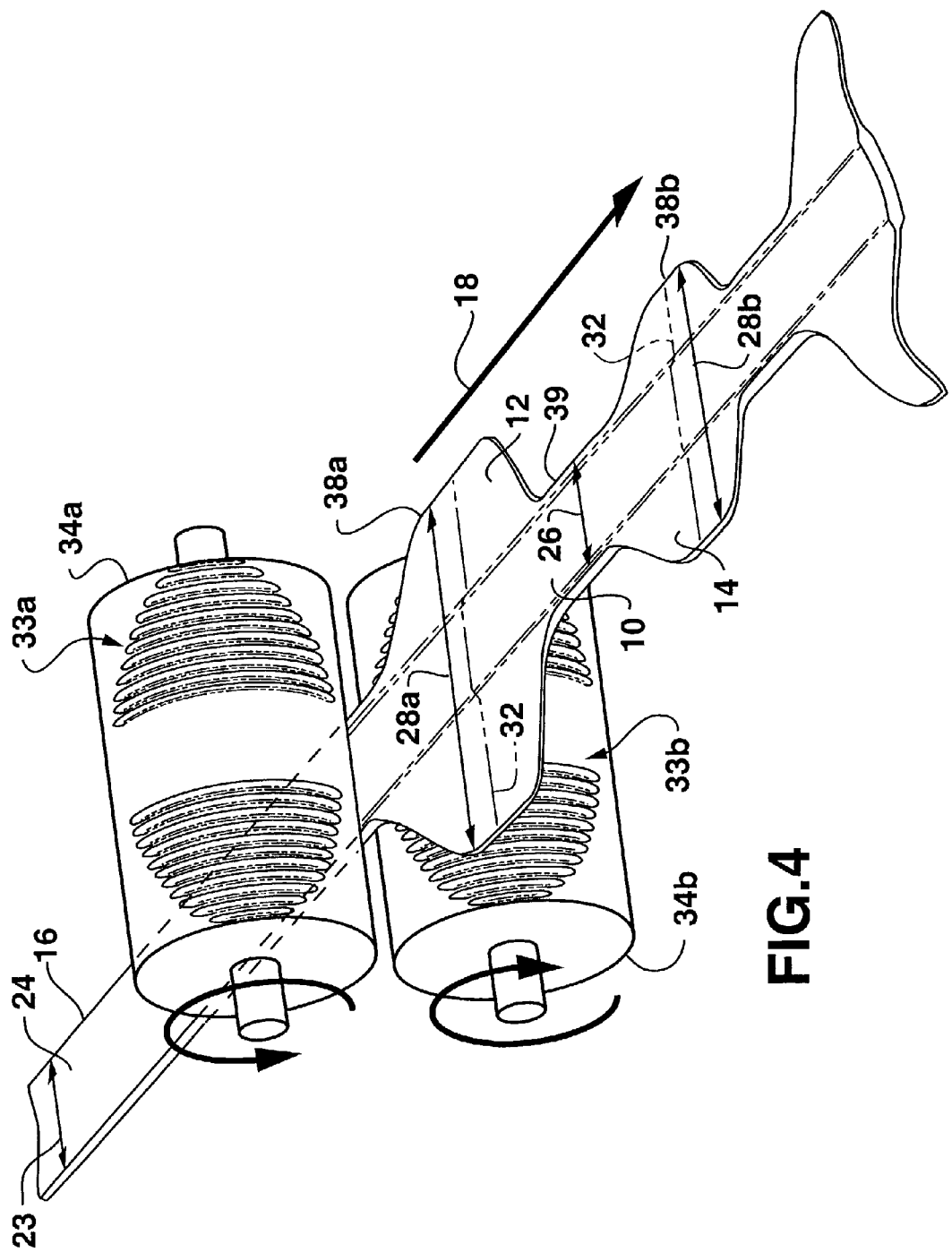
FIG. 4 is a partial perspective view of an embodiment for stretching an absorbent web material according to the invention using the roll configuration of FIGS. 3A and 3B.

FIGS. 3A–B, and 4 illustrate another embodiment wherein longitudinally asymmetric pads 10 are produced. With this methodology, the rollers 34a and 34b have at least two different patterns of intermeshing grooves. Referring to FIG. 4, the visible pattern of grooves 33a and 33b corresponds to the circumferential side of the rollers visible in FIG. 3B. These grooves 33a and 33b have a first circumferential length and extend, for example, in the cross-direction generally to the end of the respective rollers 34a and 34b. These groove sections 33a and 33b result in the stretched sections 38a having a relatively wider cross-directional width 28a. The back side of the rollers not visible in FIG. 4 have the pattern of grooves 36a and 36b shown in FIG. 3A. These grooves do not extend to the ends of the rollers and result in the second stretched section 38b having a lesser cross-directional width 28b. The longitudinal length of the unstretched portion 39 of the web strip 24 corresponds to the circumferential spacing between the groove sections 33a/33b and 36a/36b, respectively. Referring to FIG. 4, it can be seen that when the web strip 24 is subsequently cut along lines 32, a longitudinally asymmetric pad 10 is produced wherein the front section 14 of the pad has a decreased width (and increased basis weight) as compared to the back section 12. It can also be seen that the adjacent pads in the series are oppositely oriented. In other words, the front sections 14 are not all oriented in the same direction. Thus, if the strip 24 is to proceed directly to an in-line absorbent article manufacturing process, a rotate-and-place module would be necessary to rotate every other pad 10.

As mentioned, the invention is not limited to stretching or pulling the web with grooved rollers. Any suitable methodology or machinery may be employed to selectively stretch or pull defined longitudinal sections of an initial strip of web material to produce shaped absorbent pad structures according to the invention. For example, various well known configurations of tenter-frame assemblies have been used in the art for quite some time to apply a lateral (cross-direction) stretching force to webs and films. These devices generally utilize clamps to grasp the material along the longitudinal sides thereof and then drive the clamps in opposite directions as the material is conveyed through the device. Reference is made for example to U.S. Pat. No. 3,902,230 incorporated herein by reference for all purposes. It is well within the purview of one of ordinary skill in the art to modify or configure a tenter-frame type of stretching device for use in a methodology according to the present invention.

Depending on the absorbent material 16, it may be desired or necessary to "set" the stretched portions 38 prior to releasing the web from the stretching action. Certain types of generally inelastic webs will retain or hold the stretched condition without further processing or treatment. However, with other types of webs, for example elastomeric coform webs, it may be necessary to apply a heat or chemical treatment to set the stretch condition prior to releasing the web. In the embodiment where grooved rollers are used to stretch the web, the rollers may be heated to a temperature sufficient for softening and setting the elastic thermoplastic fibers. Softening of the fibers may also enhance the stretching operation by making the web material easier to stretch. Alternatively, the stretching process may take place in a steam bath or other heated temperature environment. The web material may alternately be treated with an energy source, such as microwave, ultrasonic, or ultra-violet radiation, for activating binder materials that set the stretched shape. The web material may alternatively be sprayed with an adhesive or other material to permanently or temporarily "set" or hold the web material in its stretched configuration. The adhesive may be a temporary adhesive that "releases" upon being wetted in the absorbent article such that the pad would tend to contract somewhat after being wetted. Alternatively, the stretched web may be laminated or otherwise fixed to another material prior to release from stretching. Various methods are known to those skilled in the art for setting elastomeric materials and coforms.

Figure 5:
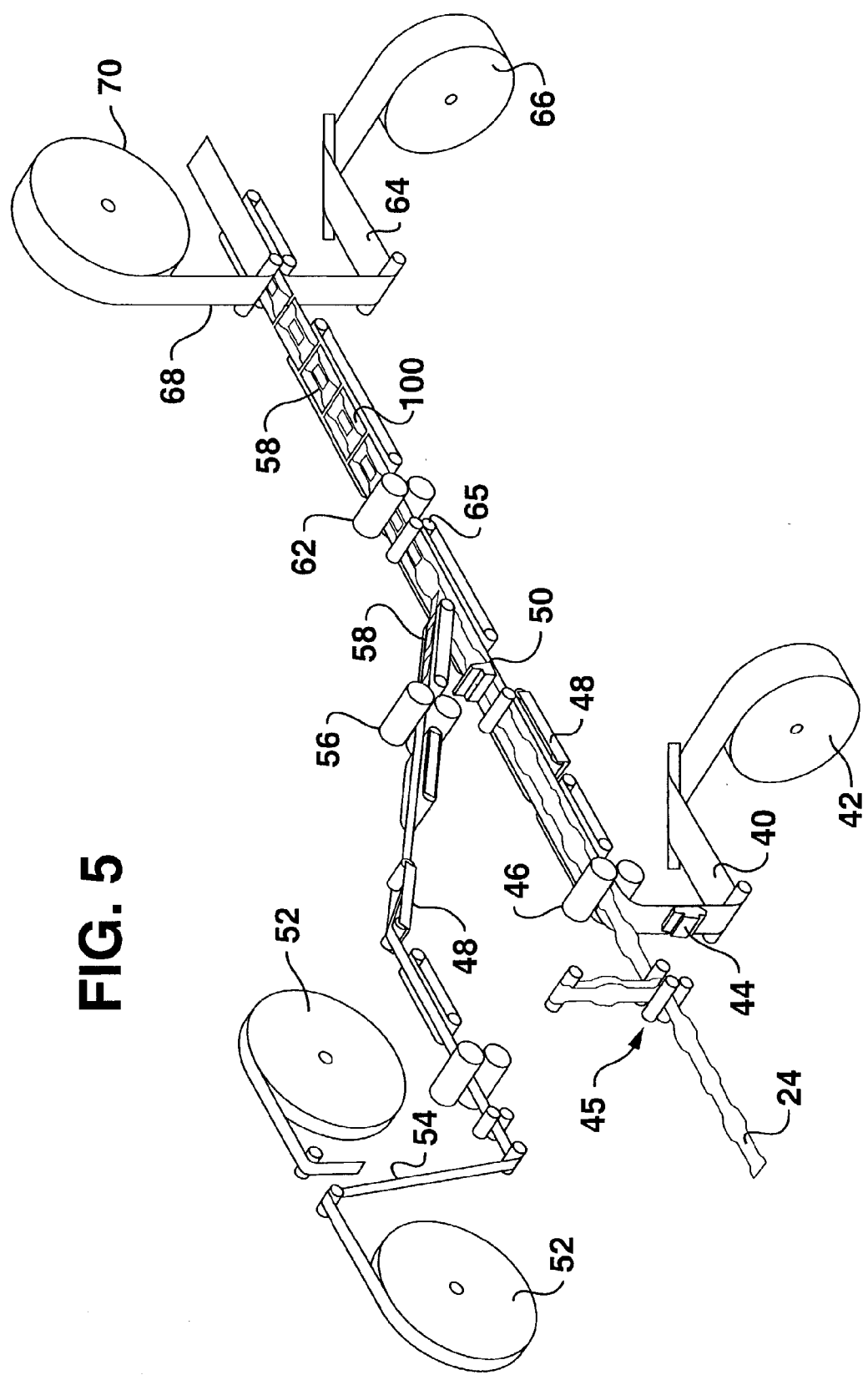
FIG. 5 is a schematic perspective view of an in-line processing method that may incorporate features of the present invention.

After defining the stretched sections in the web strip 24, the strip 24 may be conveyed directly to an in-line absorbent article manufacturing line, as depicted in FIG. 5, or may be stored in a suitable form for later use in a manufacturing line. For example, the shaped strip 24 may be stored in roll form or a stacked festooned form.

As mentioned, the web strip 24 with individual pads 10 defined therein may be incorporated directly into an in-line absorbent article manufacturing process line. A conceptual schematic representation of this process is provided in FIG. 5. It should be appreciated, however, that FIG. 5 is in no way meant to limit the in-line manufacturing process or machinery utilized in such a process, and is provided merely as conceptually illustrating an example of the invention.

Referring to FIG. 5, the web strip 24, and other material components of an absorbent article, may be appropriately guided through the manufacturing process with one or more operative guiding mechanisms 48. Various conventional web guide mechanisms 48 can be employed to keep the various webs and materials substantially aligned with respect to a machine-direction center line of the manufacturing process. For example, an absorbent web or a material supplied on a roll can tend to take on a camber if the web is level-wound or processed in any way that bends the web in the cross-machine-direction. Web guides can effectively counteract the effects of this camber. While any operative web guide may be employed, those that minimize the cross-directional bending of the web materials are preferred. For example, the web bending can be reduced by minimizing any wrapping of the various webs around an idler roll. Suitable web guides can, for example, include a camber roller FIFE guide, which is available from the FIFE Corporation of Oklahoma City, Okla.

The absorbent web strip 24 may be delivered to a phasing accumulator 45, the operation of which is well known in the art. Such an accumulator device can change the running path length of the web strip 24 to selectively advance or retard eventual positioning of the web strip 24 and pads 10 with respect to downstream processing equipment.

Additionally, the manufacturing process may also include compressing of the absorbent web material to reduce its thickness. The compressing may also increase the basis weight of the base web material, and may increase the longitudinal length and/or the cross-directional width of the web. The compressing may be substantially uniformly or non-uniformly applied across the surface of the absorbent web material. The compressing may be configured to emboss a desired pattern of embossments along the machine-direction and/or cross-direction. Referring to FIG. 5, the compressing action can be provided by a counter rotating pair of nip rollers 46. Alternative compressing devices or systems can include converging gap rollers, converging gap conveyor belts or the like, as well as combinations thereof.

An optional first tissue layer 40 from a supply 42 may be assembled to the base web strip 24. In one configuration, a bonding device such as provided by an adhesive applicator 44 and nip rollers 46, may be appropriately disposed to secure the first tissue layer 40 to the underside of the absorbent material strip 24 having the pads 10 defined therein.

At least one supplemental layer of absorbent material may be incorporated with the individual pads 10. In the embodiment illustrated in FIG. 5, this supplemental layer can be provided by pledgets 58. The pledget 58 may be substantially equal to the full length of its associated corresponding absorbent pad 10, or may be shorter than the pad 10. Likewise, the width of each pledget 58 may be equal to, greater than, or less than the smallest width dimension of the corresponding absorbent pad 10. The pledgets 58 may be defined from a suitable pledget web 54 delivered from an operative pledget supply 52 and suitably transported by an operative conveyor. A pledget cutter device 56 may be used to separate the pledget web 54 into a plurality of the individual pledgets 58 to be selectively placed onto the individual absorbent pads 10. The individual pledgets 58 can be positioned at locations that are spaced apart along the machine-direction of the first tissue layer 40 and spaced pads 10. A securing mechanism, such as provided by an adhesive applicator 50 may be used to operatively attach the individual pledgets 58 to the moving tissue 40 and pads 10. The pledget may be placed on the top or bottom of the individual pads. The pledget may also be in a shaped configuration rather than rectangular and may also be produced using the methods of the present invention. The pledget may also be applied to the web or pad prior to stretching and/or prior to cutting into individual pads.

The resulting structure may then be subjected to further conventional downstream processing operations. For example, the assembled components may be processed by a system of assembly nip rollers 65, which can enhance the desired attachments between the assembled components.

The resulting structure can then be separated into individual absorbent assemblies 100 by employing a suitable cutter mechanism, such as is represented by the cutter device 62. The assemblies 100 may be further combined with other components, as desired, for example, the absorbent assemblies 100 may be laminated to a layer of liner material 68 provided from a suitable liner supply 70. Additionally, the absorbent assemblies 100 may be combined with a layer of outer cover material 64 provided from a suitable cover supply 66. The composition of such inner and outer liner and cover materials is well known to those skilled in the art, and the invention is not limited to any particular type of material.

Figure 6:
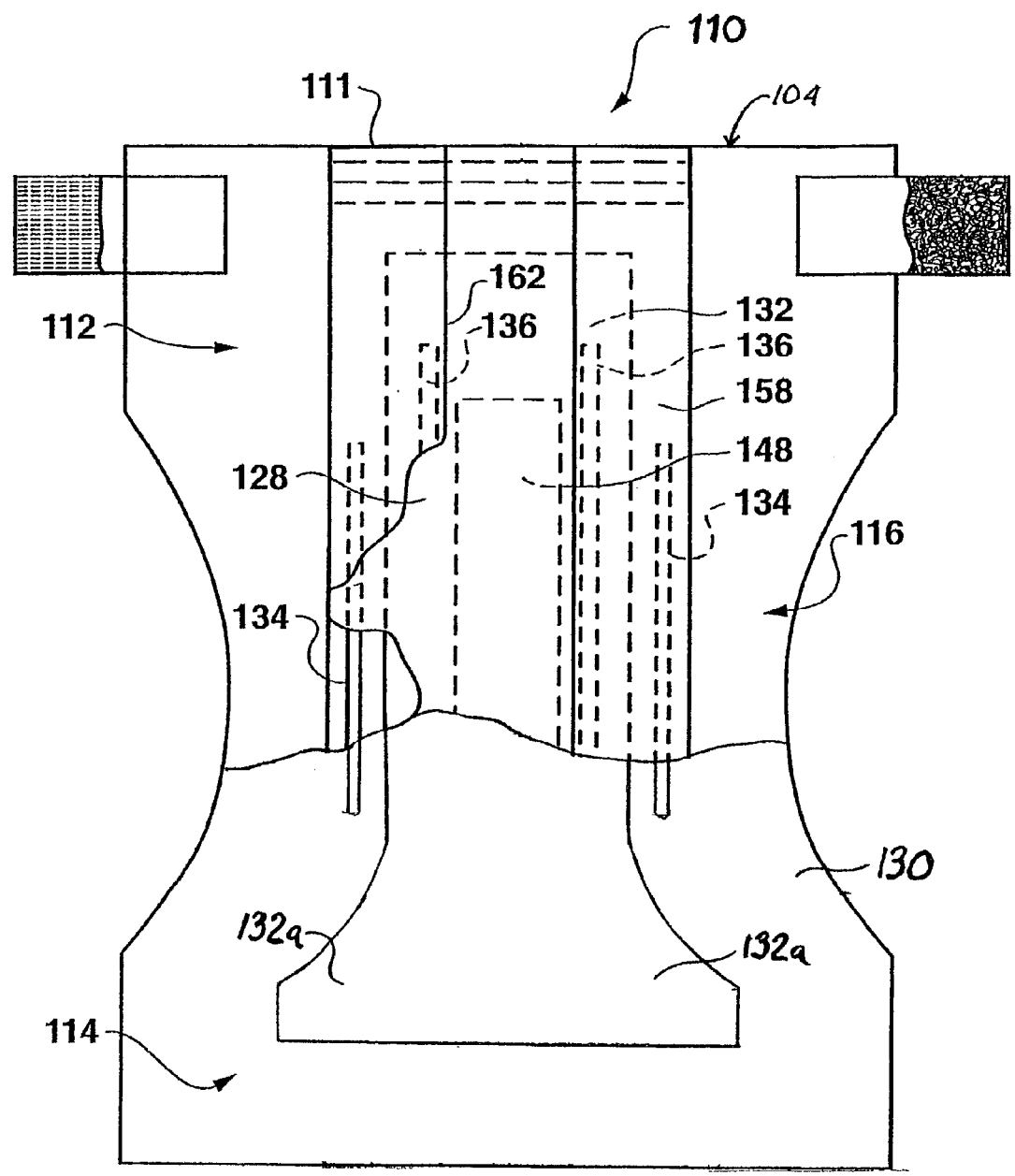
FIG. 6 is a body facing plan view of a representative absorbent article incorporating an absorbent pad in accordance with the invention.

FIG. 6 shows an exemplary absorbent article 110 incorporating an absorbent pad structure 132 made in accordance with the present invention. The article 110 is depicted as a disposable diaper having a body or chassis 104 with a front waist region 114, a back waist region 112, and an intermediate crotch region 116 interconnecting the front and back waist regions. The waist regions 112 and 114 comprise those portions of the article 110 which when worn, wholly or partially cover or encircle the waist or mid-lower torso of the wearer. In particular configurations, the front 114 and back 112 waist regions may include elastic waistband portions, such as the portion 111 incorporated into the back waist region 112. The waistbands may extend partially or completely across the waist regions.

The article 110 will typically include a porous, liquid permeable bodyside liner 128; a substantially liquid impermeable or liquid resistant outer cover member 130; and the absorbent pad structure 132 positioned and attached between the outer cover member 130 and bodyside liner 128. In certain embodiments, a surge layer 148 may be optionally located adjacent the absorbent structure and attached, for example, by way of an adhesive.

Leg elastics 134 may be incorporated along the lateral side margins of the chassis 104 outboard of the absorbent pad structure 132 and are configured to draw and hold the chassis 104 against the legs of the wearer. The use of elastic leg members in absorbent articles such as disposable diapers and training pants is widely known and understood in the art. The liner 128, outer cover 130, absorbent pad structure 132, surge layer 148, and leg elastic members 134 may be assembled together into a variety of well-known absorbent article configurations.

The article 110 may also include longitudinally extending containment flaps 158 attached to the chassis 104 outboard of the absorbent pad structure 132 and having a free side 162 with elastic members 136 extending over the absorbent pad structure so as to define a containment "pocket" along each longitudinal side of the absorbent pad 132. The use and construction of such containment flaps is understood by those skilled in the art.

Various materials are known in the art for use as the individual components of the article 110, as well as construction methods for assembling the components. An absorbent article according to the invention is not limited in any way by particular materials of construction methods.

The absorbent pad structure 132 depicted in FIG. 6 may be made according to the process described herein. The structure includes a generally rectangular shaped portion extending from the back waist region 112 and along the crotch region 116 In the front waist region 114, the absorbent pad structure 132 includes laterally extending wing portions 132a. The wing portions 132a may correspond to the stretched web portions 38 described above.

An alternate absorbent article 200 incorporating a "winged" absorbent pad structure 218 according to the invention is depicted as a feminine care product in FIG. 7, particularly as panty liner. The pad structure 218 includes a bodyside liner 212 defining a body-facing surface 232, a generally liquid impermeable baffle or outer cover 214 attached to a release liner 246 and incorporating an adhesive 236 for attaching the pad 218 to a garment. An absorbent material 216 is sandwiched between the liner 212 and baffle 214. The pad 218 includes a central portion 220 having wings or tabs 226, 228, as in generally known in the art.

Various materials are know in the art for use as the individual components of feminine care products, such as the panty liner 200, as well as construction methods for assembling the components. A feminine care product according to the invention is not limited in any way by particular materials of construction methods.

The absorbent material 216 of the pad structure 218 having longitudinally opposite wing portions 226 and 228 is particularly well suited for manufacture according to the process described herein. Reference is made, for example, to the pad structures illustrated in FIG. 1 having a generally longitudinally symmetric shape that may be used in feminine care products.

EXAMPLE

A set of circumferentially-grooved rollers was used to stretch an absorbent airlaid web in the cross direction of the web.

A web of stabilized airlaid material comprising superabsorbent, pulp fiber and binder fiber was passed through a nip between a pair of cooperating, counter-rotating, circumferentially-grooved rollers to stretch the material in the cross direction. Each of the counter-rotating grooved rollers can include an alternating series of cooperating peaks and lands. The peaks have a selected width, and a selected height. The lands have a selected width and a selected depth corresponding to the height of the peaks. The adjacent peaks that are on the same roller have a center-to-center distance. During operation, the peaks of one roll are substantially centered in the lands of the other, matched roll. An "engagement" distance between the rollers is measured as the distance from the peak provided by the first roll to the adjacently positioned peak provided by the second roll when the peaks of the first roll penetrate into the grooves of the matched, second roll. A "gap" is measured when the peaks of the first roller do not penetrate into the grooves of the second roller. In the rollers employed for the Example, the width of the peak is 0.031 inch (0.79 mm), and the width of the land is 0.094 inch (2.39 mm). The height of the peak (or equivalently, the depth of the land) is 0.09 inch (2.29 mm). The center-to-center distance between adjacent peaks that are on the same roller is 0.125 inch (3.18 mm).

An airlaid absorbent web had an initial basis weigh of 493 grams per square meter (gsm) and a density of 0.17 grams per cubic centimeter (g/cc) as measured under 0.2 psi load. The material having an initial width of 4$\frac{1}{16}$ inch was passed through the rollers at different engagement depths. In one case the material was passed through the rollers twice. The final width of the material was measured after passing through the rollers.

| Sample | Engagement ($\frac{1}{1000}$ inch) | Final Width (inch) | Basis weight (gsm) | Density (g/cc) |
| --- | --- | --- | --- | --- |
| 0 | 0 | 4$\frac{1}{16}$ | 493 | 0.17 |
| 1 | 40 | 4$\frac{3}{8}$ | 473 | 0.17 |

-continued

| Sample | Engagement (¹/1000 inch) | Final Width (inch) | Basis weight (gsm) | Density (g/cc) |
|---|---|---|---|---|
| 2 | 80 | 4¾ | 437 | 0.16 |
| 3 | 100 | 4⅞ | 443 | 0.17 |
| 4 (2× through rolls) | 100 | 6–7 | 297 | 0.14 |

A web of the airlaid was passed through the rollers with an engagement set point of ¹⁰⁰/1000 inch. The rollers were raised and lowered intermittently providing stretching in the cross direction only when the rolls were engaged. The widest part of the web with a single pad in this configuration was 4¾ inch with the narrowest portion remaining at the initial web width of 4¹/16 inch. With two passes through the rollers the widest part of the web was 6–7 inches with the narrowest portion remaining at the initial web width of 4¹/16 inch.

| Example | Engagement (¹/1000 inch) | Final Width of widest section (inch) | Basis weight (gsm) | Density (g/cc) |
|---|---|---|---|---|
| 1 | 100 | 4¾ | 451 | 0.17 |
| 2 (2× through rolls) | 100 | 6–7 | 324 | 0.14 |

It should be understood that resort may be had to various other embodiments, modifications, and equivalents to the embodiments of the invention described herein which, after reading the description of the invention herein, may suggest themselves to those skilled in the art without departing from the scope and spirit of the present invention.

What is claimed is:

1. A method for making absorbent pads from an absorbent web material, comprising:
    conveying a continuous strip of the absorbent web material along a machine direction;
    selectively stretching longitudinally defined portions of the web material in the cross direction so as to define longitudinal sections having a wider cross-direction width and decreased basis weight alternately spaced between longitudinally extending sections of the web material having a lesser cross-direction width and greater basis weight;
    releasing the web from the stretching action;
    cutting the strip of web material in a cross direction into individual absorbent pads such that each pad of absorbent web material has at least one longitudinal section of longitudinally stretched portion having a wider cross direction width;
    wherein the web material is generally elastic, said method further comprising setting the stretched condition in the web material prior to releasing the web material from the stretching action; and
    wherein the stretched condition is set by applying heat to the web material.

2. A method for making absorbent pads from an absorbent web material, comprising:
    conveying a continuous strip of the absorbent web material along a machine direction;
    selectively stretching longitudinally defined portions of the web material in the cross direction so as to define longitudinal sections having a wider cross-direction width and decreased basis weight alternately spaced between longitudinally extending sections of the web material having a lesser cross-direction width and greater basis weight;
    releasing the web from the stretching action;
    cutting the strip of web material in a cross direction into individual absorbent pads such that each pad of absorbent web material has at least one longitudinal section of longitudinally stretched portion having a wider cross direction width;
    wherein the web material is generally elastic, said method further comprising setting the stretched condition in the web material prior to releasing the web material from the stretching action; and
    wherein the stretched condition is set by applying a setting material to the web material.

3. The method as in claim 2, wherein the setting material is at least one of an adhesive and a laminating material.

4. The method as in claim 3, wherein the setting material is a temporary adhesive that releases upon being wetted.

5. A method for making absorbent pads from an absorbent web material, comprising:
    conveying a strip of the absorbent web material along a machine direction;
    selectively stretching longitudinally defined portions of the web material in the cross direction so as to define longitudinal sections having a wider cross-direction width and decreased basis weight alternately spaced between longitudinally extending sections of the web material having a lesser cross-direction width and greater basis weight;
    releasing the web from the stretching action;
    cutting the strip of web material in a cross direction into individual absorbent pads such that each pad has at least one longitudinal section of longitudinally stretched portion having a wider cross direction width; and
    wherein the web material is stretched by passing the web material between opposed heated rollers, the rollers having circumferentially spaced apart sections of intermeshing grooves defined therein in a pattern around a circumference of the rollers corresponding to the longitudinally stretched sections of the web, the rollers further imparting heat to the web material as the material is stretched.

6. The method as in claim 5, wherein the heat imparted by the rollers softens the web material thereby enhancing the stretching step.

7. The method as in claim 6, wherein the heat imparted by the rollers is sufficient to set the stretched condition.

* * * * *

UNITED STATES PATENT AND TRADEMARK OFFICE
CERTIFICATE OF CORRECTION

| | | |
|---|---|---|
| PATENT NO. | : 7,175,727 B2 | |
| APPLICATION NO. | : 10/233168 | |
| DATED | : February 13, 2007 | |
| INVENTOR(S) | : Shannon Melius | |

It is certified that error appears in the above-identified patent and that said Letters Patent is hereby corrected as shown below:

On Title Page

Title Page, item 73 Assignee reads "Kimberley-Clark Worldwide, Inc.," should read --Kimberly-Clark Worldwide, Inc.,--

Signed and Sealed this

Third Day of July, 2007

JON W. DUDAS
*Director of the United States Patent and Trademark Office*